United States Patent [19]

Guthery

[11] Patent Number: 4,704,102
[45] Date of Patent: Nov. 3, 1987

[54] METHOD OF ELIMINATING INTRA ABDOMINAL INFECTIONS

[75] Inventor: B. Eugene Guthery, Overland Park, Kans.

[73] Assignee: Geneco Inc., Lee's Summit, Mo.

[21] Appl. No.: 834,152

[22] Filed: Feb. 27, 1986

Related U.S. Application Data

[63] Continuation of Ser. No. 430,680, Sep. 30, 1982, abandoned.

[51] Int. Cl.[4] ............................................. A61J 3/00
[52] U.S. Cl. ...................................... 604/28; 604/49
[58] Field of Search ................................... 604/27–34, 604/43, 49, 54

[56] References Cited

U.S. PATENT DOCUMENTS

| | | | |
|---|---|---|---|
| 2,927,058 | 3/1960 | Minto . | |
| 3,233,609 | 2/1966 | Leucci | 604/30 |
| 3,583,404 | 6/1971 | McWhorter | 604/43 |
| 3,823,714 | 7/1974 | Waysilk et al. | 604/30 |
| 3,911,107 | 10/1975 | Krezanoski | 424/78 |
| 3,981,299 | 9/1976 | Murray | 604/43 |
| 4,235,230 | 11/1980 | Stephen et al. | 604/49 |
| 4,271,149 | 6/1981 | Winicor et al. | 424/150 |
| 4,351,333 | 9/1982 | Lazarus et al. | 604/29 |
| 4,402,937 | 9/1983 | Densinger et al. | 424/80 |
| 4,419,094 | 12/1983 | Patel . | |
| 4,539,234 | 9/1985 | Sakamoto et al. | 604/265 |

OTHER PUBLICATIONS

Kottasz, S., *Orv Hetil* (Hungarian) (5 Jan. 75), 116(1) (pp. 25–26).
Hutinel, P. et al., *La Nouvelle Presse Medicale* 7, n° 36, (Oct. 21, 1978), pp.3250–3261.
Akiyama, H. et al., *J. of Urology*, vol. 121 (1979), pp. 40–42.
Sharpe, J. R. et al., *Urology* (U.S.), 1981, 17(4), pp. 335–338.
Harper, W. E. S., *Br. J. Urol.* (Scotland), 1981, 53(5), pp. 443–438.
Sharpe, J. R. et al., *J. of Urol.* (U.S.), Feb. 1982, 127(2), pp. 255–256.
Seal, D. V. et al., *The Lancet*, Jan. 9, 1982, pp. 89–91.
Merimsky et al., *Br. J. Urol.*, Australia, 1984, (53)4, pp. 330–332.

Primary Examiner—C. Fred Rosenbaum
Assistant Examiner—Denise Whelton

[57] ABSTRACT

A method of irrigation of a body cavity, promoting asepsis, in which an irrigant solution, preferably a solution of iodine, is introduced into an abdominal cavity, retained within the abdominal cavity until asepsis is achieved, and drained from the abdominal cavity. Preferably, the solution includes a local anesthetic and a binding agent such as glycol. A catheter apparatus particularly adapted for implementation of the irrigation method comprises a drainage means and an independent irrigation means. In the catheter, a first valve assembly is connected to the drainage means so that the drainage of fluid from the abdominal cavity may be selectively regulated. A second valve assembly provides for selective opening of the irrigation means to allow introduction of the irrigation solution into the abdominal cavity. A kit comprising the catheter apparatus and auxiliary equipment, including a reservoir for the irrigant, a valve actuator tool and a syringe for use with a catheter retention means, provides for implementation of the treatment method.

6 Claims, 12 Drawing Figures

METHOD OF ELIMINATING INTRA ABDOMINAL INFECTIONS

CROSS-REFERENCE TO RELATED APPLICATIONS

The present application is a continuation of Ser. No. 430,680 entitled Method of Eliminating Intraabdominal Infection, filed Sept. 30, 1982, now abandoned.

BACKGROUND OF THE INVENTION

The present invention relates to prevention of intraabdominal infections and especially to prevention of infections associated with indwelling catheters.

Although certain abdominal cavities are typically low in bacteria count and are classified as infection free, the use of conventional intra-abdominal instrumentation, such as catheters, in these cavities is often accompanied by a large number of infections (that is, a high relative bacteria count). Of such infections, those of the urinary tract are the most common, accounting for as many as forty percent of all nosocomial infections. A nosocomial infection is an infection acquired during hospitalization which was not present or incubating when the patient was admitted to the hospital. The majority of urinary tract infections are associated with indwelling urethral catheters or other types of urethra and bladder penetrating instrumentation. Infections resulting from urinary catheters have been responsible for excess mortality as well as morbidity among the catherized population and have been the subject of numerous, and most often at least partly unsuccessful, attempts to control or prevent same.

The potential sequelae of such urinary tract infections include: gram-negative rod bacteremia; anti-microbial toxicity during treatment; acute and chronic pyelonephritis; chronic bactiuria; perinephric, vesical and urethral abscesses; bladder and renal stones; bladder cancer; renal failure and death. These complications result in substantially increased costs for treatment.

The uninstrumented bladder is usually sterile or very low in bacteria count. Passage of a catheter through the urethra offers a portal for organisms that may overwhelm the bladder's defenses. One source of urethral organisms are those organisms that are carried into the bladder by insertion of the catheter. Catheters not removed immediately but left indwelling offer additional opportunities for entry of bacteria. A frequent source for the infecting organisms is endogenous from the patient's own fecal or urethral flora. Once these organisms are in the periurethral area they may travel into the bladder between the urethral mucosae and the external catheter surface. An additional source for the infection is exogenous contamination by hospital personnel at the junction of the catheter and the collecting tube or drain hose on the collecting bag. Thus, attempts to disinfect the collecting bag reduce but do not eliminate these nosocomial infections, especially since the infections are more frequent in women apparently due to contamination of the periurethral area.

None of the prior art catheters and methods have been fully successful in preventing or controlling the urinary tract infections associated with such catheters.

There follows a general outline of some of the attempts that have been made at preventing infections resulting from catheterization, especially bladder infections.

As early as 1928 certain physicians and theorists advocated closed drainage catheter systems, that is a collection bag is connected to a drainage tube associated therewith in a sealed or fused manner to prevent breaking into the tube and thereby allowing bacteria or other microorganisms to gain entry into the interior of the catheter and from there to migrate to the bladder. The closed drainage systems did not become widespread until the early 1960's. The incidence of bactiuria is substantially lower in closed systems as compared to open systems, however, infections do still occur. A more recent closed system concept includes a technique wherein the catheter is taped to the collecting tube so that it can be visually determined if the junction has been inadvertently opened, that is the tape is broken, and steps can be taken to correct the problem.

Antibiotics have also been frequently utilized as a prophylaxis to infection in the bladder occasioned by catheterization. In particular, antibiotics are given to catheterized patients at or prior to catheterization and continuing while the patient is catheterized and before the actual development of urinary tract infections so as to prevent or postpone an infection. Careful analysis of data from such treatments suggests that the use of antibiotics may result in lower rates of infection and fewer febrile episodes in catherized patients. However, serious disadvantages associated with the use of antibiotics include allergic or toxic reactions to the antibiotic, selective increases in resistant organisms and increased cost. In particular, strains of microorganisms which are resistant to the particular antibiotics may multiply as well or even better than if no antibiotic were used.

Antibiotic treatment has also been utilized to treat organisms once infection has taken place. When the catheter is to remain indwelling for a long period of time, such treatment is normally not successful for the patient will become infected again after an initial infection has been controlled. If the catheter is to be removed within seventy-two hours, it is generally accepted that such treatment will probably be successful with the limitations and hazards of prophylactic antibiotics, provided that an appropriate antibiotic is chosen which is effective against the particular infecting microorganism.

Another type of treatment has been directed to preventing microorganisms from entering the urethra and migrating to the bladder outside the catheter. Such treatments often include the use of antiseptic ointments such as polymycin B or organically complexed iodine solutions such as are marketed under the name Betadine. Application of an ointment to the periurethral space or on the outside of the catheter at the time of catheterization will often delay the development of nosocomial urinary tract infection; however, daily application of an ointment to the urethra and external region surrounding the catheter, once the catheter is in place, is normally detrimental rather than preventive and often results in an increased incidence of infections.

Intermittent catheterization is a technique which has been used most successfully in patients with neurogenic bladders. In this technique a small bore catheter is inserted 3 times daily. This is not practical in a hospital population due to the substantial amount of time required to effect each catheterization.

Another method utilized in the past has been to have a potential bladder infection patient ingest urine acidifying agents, such as mandelamine. The mendelamine is metabolized to formaldehyde in the kidney which then enters the bladder and lowers the urine pH to less than 6.0. This treatment has been most successful in preventing recurrent infections in a non-catheterized patient population. Such treatment often fails in catheterized patients because there is inadequate retention time in the bladder to retain formaldehyde in the bladder which is continuously draining.

Various types of bladder irrigations have been attempted to prevent or eliminate infection accompanying catheterization. Bladder irrigation with antimicrobial agents is probably the most widely practiced attempt to prevent urinary tract infection subsequent to catheterization. Since entry of bacteria was not preventable in the early techniques wherein the catheter systems were open, it was postulated that an irrigation with antimicrobial solutions would prevent multiplication of organisms and possibly the development of bacteriuria. Irrigation in open systems by continuous and intermittent methods have both been used. An intermittent irrigation often included the addition of a solution including the antimicrobial agent into the bladder through the catheter drainage lumen. The lumen was then clamped and the solution retained for a short time. This technique was used for prevention of bacterial infection in patients with indwelling urinary catheters and those receiving intermittent catheterization. This method was not greatly effective in preventing bacituria.

A continuous irrigation system, using an indwelling triple-lumen catheter, was originally designed to allow continuous flushing and to thereby prevent obstruction of the catheter by blood clots following surgery of the genitourinary tract. For prevention of infection, an antimicrobial solution was dripped into the inlet port of the catheter and drained through a second lumen. The third lumen is for inflation of the balloon at the tip of the catheter which secures proper placement. This system allows continuous flow of the flushing or irrigant solution into the bladder. With this system, contact of the bladder with the irrigant is restricted to the area surrounding the catheter tip. Unless the antimicrobial solution comes in contact with the entire bladder mucosae this therapy will fail to prevent urinary tract infections in the untreated areas.

Various other attempts have been made to design a catheter structure that will actively or passively prevent bladder infections. For example, certain structures have been designed to facilitate the drainage of urine from the bladder. Other catheters are designed to irrigate the periurethral area, especially the bladder and to empty directly into a drainage lumen so as not to expand the bladder with irrigating fluid such that the bladder mucosae is entirely directly exposed to the fluid during the irrigation.

Another catheter designed to overcome infection comprises a silver rod which slowly releases silver within the bladder to kill organisms through action of silver. This treatment only selectively kills certain organisms not resistant to oligodynamic action, is bacteriostatic rather than bacteriocidal and is expensive.

In general, multilumen catheters have previously been developed for continuous irrigation of the bladder. However, these catheters have not been entirely successful, theoretically for several reasons. First, continuous irrigation, as was mentioned above, has not resulted in a thorough exposure of the bladder wall to the antiseptic, or antibiotic in the irrigating solution. Secondly, the opening of the catheter system to the environment as required for routine maintenance during continuous irrigation may allow bacteria into the catheter system, thus counteracting any positive effects resulting from the continuous irrigation itself. In fact, reinfection may make continuous irrigation less effective than no irrigation at all. Thirdly, the irrigants used have been of questionable effectiveness in preventing or eliminating the infections, which result from a wide variety of bacteria species and other microorganisms.

Tidal drainage irrigation techniques, where the outflow line is clamped until the bladder has reached a physiologic volume (about two hours at an irrigant flow rate of one milliliter per minute), increases contact time and the distribution of the irrigant. Painful bladder contraction that may occur with some types of irrigation can be prevented with tidal drainage. However, the narrow outflow lumen in the three-way catheter is susceptible to clogging and, despite the increased effluent flow, may require disconnection of the closed system to clear an obstruction. Such opening of the closed system allows entry of microorganisms and is considered undesirable.

Various techniques utilizing intermittent irrigations have also been utilized to lower the incidence of bladder infections in catheterized patients. For example, addition of a neomycin solution following catheterization was tried but found to have little or no effect on decreasing the incidence or urinary tract infections. Furthermore, a greater percentage of infections related to more resistant pathogens was seen in patients receiving neomycin irrigations. In particular, there was an increase in the number of infections by Pseudomonas aeruginosa and Group D streptococci (Enterococcus).

In single catheterizations irrigation by chlorhexidine digluconate (0.02%) has been found to be somewhat effective in reducing the incidence of infections. Also, in patients with existing infections, irrigation twice daily with chlorhexidine digluconate (0.02%) will decrease bacterial counts in the urine but has not been found to sterilize the urine. Thus, such treatment is not recommended for existing urinary tract infections. A 4% solution of such chlorhexidine is required for immediate bacteriocidal effect but solutions that are greater than 0.02% tend to be irritating to the bladder.

Acetic Acid (0.025%) is probably the most frequently used conventional intermittent irrigation solution. It is effective in decreasing debris. However, controlled studies using acetic acid as an irritant have failed to show decreased bacterial counts in patients with indwelling catheters.

Silver nitrate has also been tested as a intermittent irrigation. The patients of the tests were asked to retain the solution for thirty minutes for complete batericidal action. The solution caused severe pain and the maximum time a patient could retain the silver nitrate in the bladder was two minutes.

Further, polyvinylpyrrolidone-Iodine (10%) solution has been used in experimental animals as a bladder irrigant to prevent infections. A moderate to severe erosive cystitis occurred in all animals suggesting that such therapy would not be useable in humans.

In open catheter systems continuous antimicrobial bladder irrigations have been somewhat effective in decreasing the overall rate of urinary tract infection. Both continuous acetic acid at 0.25% and neomycin/polymyxin B irrigations have also been somewhat effective in delaying the onset of bacteriuria in open catheter systems. Continuous irrigation with nitrofurazone has been utilized but has been shown to be inferior to neomycin/polymyxin B in preventing bacteriuria in catheterized patients, and produced a significant incidence of hematunia and is not recommended for use because of its relative ineffectiveness and substantial toxicity.

In closed catheter sytems, continuous antimicrobial irrigations have not been demonstrated to decrease the incidence of urinary tract infection. Irrigations with either neomycin alone or in combination with polymyxin B have not significantly altered the rates at which bacteriuria occurs. Chlorhexidine solution administered by continuous irrigation has not been shown to be an improvement over no irrigation.

Continuous bladder irrigations for eradication of existing infections have been of limited value or no value. Irrigation of an open catheter system with neomycin/polymyxin B has been found to be ineffective in sterilizing the urine, although most infecting organisms were sensitive to the antibiotics. In fact, superinfection with resistant organisms occured in most cases. In patients with severe fungal cystitis or fungus balls limited to the lower urinary tract, continuous irrigation with Amphotericin B is effective but Amphotericin B is not effective against bacteria.

In the process of inhibiting a portion of the organisms from gaining entry into a catheterized system, antimicrobial irrigations exert a selective pressure which increases frequency of resistant organism such as Entemococcus, Pseudomonas, Proteus and Caudiat.

There has not been found conclusive evidence in the medical literature that prophylatic irrigations with any solution will decrease urinary tract infection rates in closed catheter drainage system. Prophylatic irrigations seem to be ineffective and may be a predisposing factor toward contamination of the system and subsequent urinary tract infections.

Therefore, the conventional methods involving continuous irrigation of an abdominal cavity to control infection have been ineffective. In addition, other problems have been associated with the previous methods. First, the equipment necessary to maintain a continuous irrigation is cumbersome and restricts patient mobility and comfort. Secondly, continuous irrigation equipment requires frequent monitoring by health services personnel to ensure proper irrigation. Thirdly, the prior art irrigation equipment is subject to patient tampering causing both reinfection problems and potential blockage of the fluid so as to prevent drainage. Fourthly, prior art continuous irrigation does not readily allow for the occasional treatment of the patient's abdominal cavity with medications such as an anesthetic to control spasms and maximize patient comfort. And fifthly, prior art continuous irrigation equipment is not readily adapted for treatment of other troublesome infections of the abdominal cavity (such as from cystoscopies, cystitis, and, in particular, pyocystitis).

Another problem associated with previous attempts to prevent urinary tract infections has been that a totally satisfactory solution for killing and preventing growth of microorganisms was not recognized. Various solutions were used with varying effects. For instance, use of an antibiotic solution, as previously discussed, often resulted in prevention of some bacterial growth when the bacteria was effected by the antibiotic; however, other resistant bacteria will be immune to a particular antibiotic and these continue to grow. Also yeast and certain other non-bacteria microorganisms are normally not affected by antibiotics.

Other attempts to find a suitable solution or irrigant to make abdominal cavities antiseptic, especially the bladder, have not been satisfactory as some of the irrigants, silver nitrate for example, are very effective in killing microorganisms, but are too painful and irritating to the patient for routine use. Other irrigants, while effective in killing microorganisms are harmful or deadly to tissue or cannot be used internally for reasons of toxicity. For instance, some of the organic chlorides are toxic. Attempts have been specifically made to try to use standard povidone-iodine solutions as irrigants; however, such solutions have often resulted in severe problems. For example, studies on rats suggest that povidone-iodine irrigations may cause erosive cystitis. Theoretically, the problem with povidone solutions, and other organic iodine complexing compounds, is that, for example, a standard 10% povidone solution has about 10,000 parts per million (by weight) complexed iodine and about one part per million free iodine (depending on temperature, etc.) Solutions of one part per million free iodine should be nontoxic; however, there is a relatively fast working chemical equilibrium function in the povidone solutions which replaces the free iodine almost immediately upon its use. Therefore, the entire 10,000 parts per million of complexed iodine in such a solution are readily and quickly available as free iodine. A solution having 10,000 parts per million of free iodine can cause serious tissue damage and may be fatal if used internally in a human. Also, the povidone may cause decomposition of catheters used in conjunction with the irrigant. Other previously discussed solutions such as acetic acid and neomycin/polymyxin B solutions have been shown ineffective in killing bladder infection in catheterized patients. As a result of the previous problems, the prior art does not disclose the use of an unquestionably safe, effective irrigant in bladder irrigation.

Certain particular problems with infection occurs in other parts of the abdominal cavity. For example, peritonitis is one of the commonest complications of peritoneal dialysis. As many as 46% of patients undergoing dialysis have been shown to have an occurance of peritonitis before the end of the first year of treatment. Attempts at prevention of peritonitis have been unsuccessful, thus leaving infection a major threat to dialysis patients.

Similar problems persist in colon surgery. Although infection is not a problem in the normal colon, when the colon wall is disturbed during surgery, infection may set in. The prior art does not disclose an effective method of preventing such infection.

Accordingly, in order to stop the proliferation of infections in abdominal cavities, especially due to instrumentation such as catheterization, a previously unsatisfied need exists for an effective method of control of intra-abdominal cavity infections, and a catheter device adapted to implement such a method of treatment.

OBJECTS OF THE INVENTION

Therefore, the objects of the present invention are: to provide an effective method of treatment of a human abdominal cavity to control the growth of microorganisms within the cavity and thus to eliminate infection therein; to provide such a method utilizing agents which are not generally harmful or painful to the patient being treated; to provide such a method for control of abdominal cavity infections, especially nosocomial infections in patients with indwelling intraurethral Foley type catheters; to provide a catheter especially suited for use with such a method of treatment of abdominal cavity infections; to provide such a catheter especialy adapted for use in the urinary tract; to provide such a catheter device characterized by multiple internal lumina for drainage and irrigation, wherein each such lumen is associated with a valve assembly adapted for use with the treatment method; to provide such a catheter device which is relatively easy to use in conjunction with the treatment method; to provide such a catheter device in which the valve assemblies are generally tamperproof to avoid unintended interference with the treatment method; to provide a catheter system which is "closed" to microbiological entry thereinto yet which is flexible to allow connection to irrigant sources without entry of microorganisms; to provide such a system wherein an antiseptic irrigant passes from a source through the bladder into a catheter collection bag so as to sterilize both the bag and the bladder; to provide an irrigant fluid which is safe, effective in killing microorganisms and well tolerated by the body; to provide such a fluid which has a broad range of microbiocidal activity against bacteria, yeast and the like with relatively little or no resistance; to provide such a fluid wherein the strength of active microbiocides therein is potentiated by addition of additional components; to provide such a fluid having anesthetic properties; to provide a kit including such a catheter to be utilized in such a method of controlling infections; and, to provide a catheter and such a kit which are relatively easy to manufacture, easy to use and particularly well adapted for the intended use thereof.

Other objects and advantages of this invention will become apparent from the following description taken in conjunction with the accompanying drawings wherein are set forth, by way of illustration and example, certain embodiments of this invention.

SUMMARY OF THE INVENTION

A method of treatment of infections of human abdominal cavities is provided. The method comprises: the introduction of an antiseptic solution, hereinafter also referred to as an irrigating solution or irrigant, into the abdominal cavity; retention of a concentration of the irrigant within the abdominal cavity until at least partial and normally total asepsis is reached; and, thereafter, drainage of the irrigant solution from the abdominal cavity.

The preferred antiseptic solution is an aqueous solution of iodine and potassium iodide containing a concentration of iodine ranging from 0.0002% to 7% by weight. One suitable starting solution which may be aqueously diluted in Lugol's Solution which is an aqueous solution containing 5 grams of iodine and 10 grams of potassium iodine per 100 milliliters of water. Also, normally the percentage by weight of potassium iodide will be approximately twice that of the iodine by weight but a wide ratio of potassium iodide to iodine is possible. The effectiveness of the solution comprising iodine varies somewhat proportionally with the retention period above a minimum concentration level and with the amount of residual urine in the bladder, for example, a solution having a concentration of iodine in the approximate range from about 0.01% to about 0.02% by weight has been found in vitro to be effective in a period of approximately one minute in substantially killing all of the common pathogenic microorganisms which result in infections in human abdominal cavities, especially the bladder, including various bacteria and yeasts, when such microorganisms are at a concentration of ten million ($10^7$) organisms per milliliter at body temperature.

A somewhat higher concentration of iodine is required when used in the bladder as compared to in vitro, residual urine in the bladder has a slight inactivating effect on the iodine. A concentration of 0.05% iodine by weight in an irrigant solution will normally overcome the effect of the urine, yet remain an effective microbiocide when used as an irrigant of the bladder.

In patients undergoing urinary tract catheterization the method of treatment in accordance with the present invention is to catheterize the patient and, thereafter, to irrigate intermittently with a suitable irrigant solution. Normally, the patient will be initially irrigated immediately following the cessation of the flow of urine from the catheter at the time of catheterization. The bladder is thereafter irrigated on a periodic basis. For example, the irrigation can be timed to occur once every eight hours immediately preceding emptying of the collection vessel associated with the catheter. The irrigating solution, preferably an iodine solution, is then retained within the bladder for a period of approximately one minute. A volume of about 250 milliliters of 0.05% iodine by weight in an aqueous potassium iodide solution should be effective in most adults; however, it is foreseen that the volume of solution could vary over a range from as low as 20 to 30 milliliters or less for children and quadraplegics to about 300 milliliters where an adult patient may begin to suffer discomfort and have the urge to void. Patients with a cystocele may require up to 500 milliliters. It is preferred that the entire mucosae of the bladder contact the irrigant so as to ensure complete sterility throughout the bladder, therefore a sufficient volume of irrigant to stretch the folds of the bladder wall is preferable. It has been found that this can be accomplished by placing a bag in flow communication with the bladder while being held 30 inches above the bladder and preventing drainage from the latter.

If the patient suffers from an infection prior to catheterization, the catheter apparatus and method are used to effect a rapid series of irrigations. The catheter is placed in the cavity and the irrigation process is repeated until the effluent appears clear of debris and has an iodine tint, indicating that no further oxidation of iodine is occuring. In particular, two bladder infections, pyocystitis and acute or recurrent cystitis may be treated in this manner.

Further, immediately prior to indwelling catheter removal from the patient, it is contemplated that a final aliquot of irrigant is to be introduced into the bladder (sufficient to initiate a desire in the patient to void) and retained therein, the balloon is retracted and the catheter is thereafter removed while the irrigant is retained within the bladder. Following the catheter removal, the patient then voids, thus discharging the irrigant from the bladder. In passing through the urethra, the irrigant promotes asepsis thereof, thus reducing the chances for post-catheterization infection from a contaminated urethra. Asepsis or sterilization of the bladder may be determined by sampling urinary output and microscopically inspecting the sample for bacteria, by cultering the urinary sample or by other conventional methods of making such determination.

Treatment of a patient about to undergo surgery of the colon would involve insertion of the catheter into the colon and an irrigation, preferably with a iodine solution, similar to that described for the bladder following a thorough enema such that the colon would be left both clean and generally sterile.

In patients undergoing peritonetal dialysis, the antiseptic may be added in the dialyzing fluid. Thus, the irrigation is achieved during the dialysis. Iodine solutions with concentrations in the nature of one part iodine to 200,000 parts by weight total solution may be effective in conjunction with dialysis since retention of the dialyzing fluid are normally relatively long. When iodine solution is used during dialysis, care must be taken to utilize a sufficiently low level of iodine such that the body does not over absorb iodine so as to disrupt function of the thyroid gland. This lower level may be accomplished by potentiating the solution as discussed below.

In routine cystoscopies, the irrigant may be introduced through the optical instrument and retained in the abdominal cavity during the procedure. Irrigant may also be introduced through a Robinson catheter after instruments are removed from the bladder and urethra. These irrigations reduce incidence of infection due to the instrumentation.

An anesthetic suitable for internal use in an amount to anesthetize the region to be treated may be added to the antiseptic solution to maximize patient comfort and to control spasms of the bladder. The anesthetic is preferably chosen from the cain or azo groups suitable for use on human tissue, for example, pyridium, in the amount of about 1% by weight of the irrigant. Thus, anesthesia would occur during the irrigation.

The iodine may be potentiated by agents such as di-2-ethylhexyl sodium sulfosuccinate (sold under the trademark Aerosol OT) and oxidation-reduction systems such as ferric chloride-ferrous chloride. The increased germicidal efficiency of iodine in the presence of these agents allows for solutions containing lower iodine concentrations to be used. Effectiveness of an iodine solution as a bactericidal agent has been shown to be improved by a factor of up to ten times by addition of such potentiating agents.

Glycol is advantageously added to the irrigant solution. The glycol tends to adhere to the walls of the abdominal cavity being irrigated and to also urge iodine in the irrigant to remain in contact with the wall after the majority of the irrigant is drained from the cavity. A solution containing about 20% by weight of glycol has been found to be very effective for this purpose, although a wide range of percentage of glycol in the irrigant is effective for this purpose. It has been found that higher percentages of iodine in solution can be used without injury to tissue when glycol is included in the solution.

The catheter device for use with the above methods comprises a flexible tube housing a plurality of internal lumina. One lumen provides drainage from the abdominal cavity of waste fluid or irrigation fluid. A second lumen provides a passageway for the introduction of irrigation solution into the abdominal cavity. The first and second lumens are preferably separate channels but may be joined therealong to form a single channel in some embodiments. A third lumen is alternatively provided for communication with a balloon retention means to selectively expand and deflate same.

Each lumen is associated with a separate valve assembly for operably blocking or alternatively allowing flow through a respective lumen. Selective actuation of the valve assemblies in conjunction with one another permits application of the treatment methods described herein.

The drainage lumen is associated with a valve assembly whereby drainage of irrigant fluid from the abdominal cavity may be regulated and is adapted for connection to an extraabdominal fluid collection system. The antiseptic properties of the irrigant fluid also sterilize the fluid collection system when drained into same.

The irrigation lumen is associated with a valve assembly whereby such irrigation lumen may be operably opened for the introduction of irrigant into the abdominal cavity, especially the bladder, and closed between treatments to prevent the introduction of infection. The irrigation valve assembly is adapted for a locking type of connector, for example, a Luer-lok connector, to a reservoir of irrigant. The irrigation lumen preferably retains antiseptic irrigant therein between irrigations such that infectious bacteria and other microorganisms are killed and thereby effectively prevented from passing through the irrigation lumen from the irrigation valve assembly to the abdominal cavity between irrigations. The retaining of the irrigant in part of the lumen is thus an effective barrier to infection and the system thus functions as if same were completely "closed" while allowing disconnection of the irrigant source from the valve assembly to allow the patient to have greater freedom of movement.

The retention lumen is associated with a balloon as the retention means. The retention lumen is connected to a valve assembly whereby a fluid, such as air, is introduced into the balloon for inflation and allowed to drain for deflation. The inflation valve assembly is sized and shaped for connection to an inflation syringe but not the irrigant reservoir to prevent accidentally mistaking one for the other.

The valve assemblies are tamperproof, that is, designed so as to not be easily operated by a patient being catheterized thereby; thus avoiding unintended actuation of the valves and interference with the treatment by the patient or others not responsible for the catheter. Each valve assembly is actuated by an actuator tool which is removable from the valve thereby rendering the valve tamperproof when the tool is removed. Preferably, the same tool fits and operates all of the valves associated with the catheter. The valve assemblies are also preferably color coded to facilitate catheter use without error or confusion. Also, the size and relative positions of the valves are such as to promote ease of use without loss of utility.

A kit is provided for implementation of the irrigation method, preferably for irrigation of a bladder. The kit comprises: the catheter device, for drainage of fluid from the bladder and having a retention balloon and an internal lumen providing a means for introduction of an irrigation solution into the bladder; the actuator tool for selective actuation of the valve assemblies; an irrigation reservoir for holding irrigant solution and for intermittent attachment to the irrigation valve assembly and for release of the irrigant solution therefrom into the irrigation lumen and bladder; a balloon expanding syringe for attachment to a balloon valve assembly and for inflation and deflation of the retention balloon; and a valve assembly adapted for connection of the irrigant reservoir to a container of irrigant.

The drawings constitute a part of this specification and include exemplary embodiments of the present invention and illustrate various objects and features thereof.

DETAILED DESCRIPTION OF THE PREFERRED EMBODIMENT

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 in FIGS. 1 through 10 generally designates a first embodiment of a catheter apparatus according to the present invention. The description herein generally refers to a catheter apparatus 1 having a functional position wherein a portion of the catheter apparatus 1 extends from an abdominal cavity of a user into the extra-abdominal environment and the catheter apparatus 1 is an integral part of an abdominal cavity irrigation and drainage system. The following detailed description applies both when the catheter apparatus 1 is partly positioned within the abdomen of a patient or user thereof and when in a non-operative position outside the abdomen.

Figure 1:
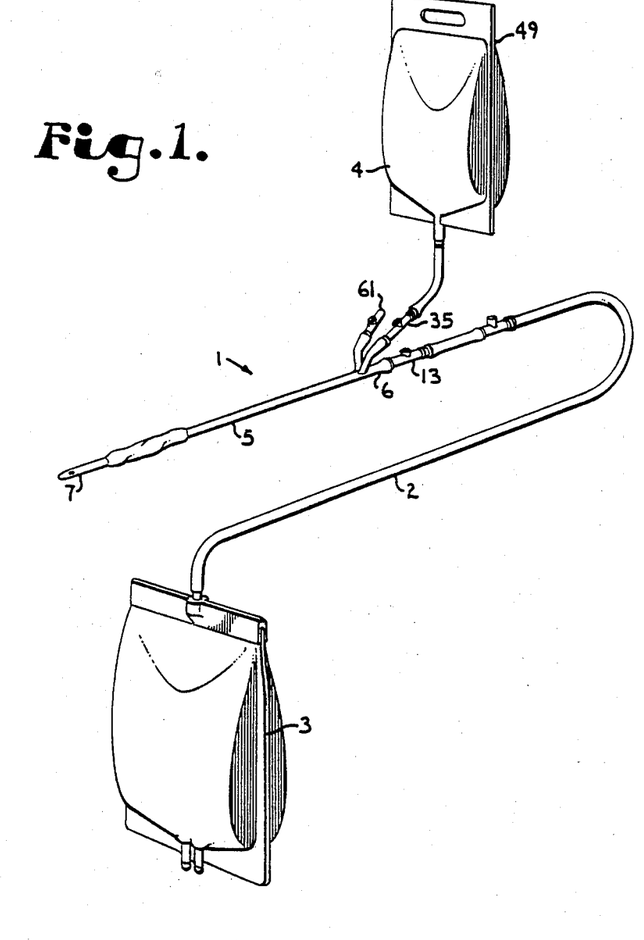
FIG. 1 is a perspective view of a catheter apparatus according to the present invention and illustrating an irrigation solution source and a drainage collection bag associated therewith.

Illustrated in FIG. 1, is the catheter apparatus 1 fluid flow connected through a drainage line 2 to a drainage collection bag 3 and also flow communicating with an irrigation source 4.

Figure 5:
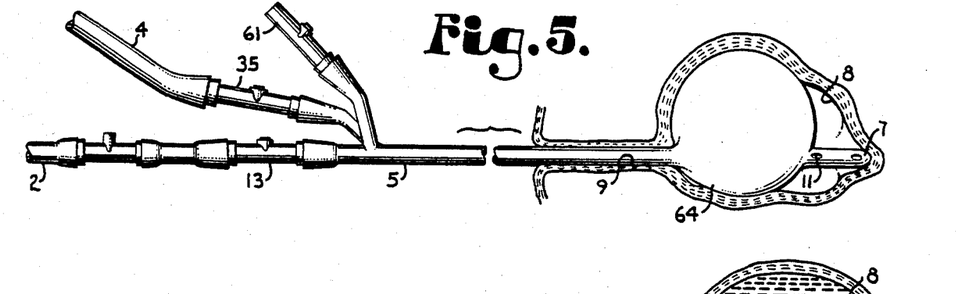
FIG. 5 is an enlarged and fragmentary side elevational view of the catheter apparatus with the distal portion thereof positioned in a bladder, with a balloon portion thereof inflated, and with an irrigation source connected thereto immediately preceding administration of an irrigant into the bladder.

The catheter apparatus 1 comprises an elongate flexible tube 5 adapted for insertion through an abdominal orifice and into an abdominal cavity and having a proximal end 6 and a distal end 7. Preferably, the extended flexible tube 5 is composed of a silicon-rubber material which is relatively inert in an abdominal environment and is relatively comfortable to the patient during use. In FIG. 5, the catheter apparatus 1 is shown positioned within a human bladder 8 and extending through the urethra 9 associated with the bladder 8. It is foreseen that the catheter could be utilized in other abdominal cavities such as the colon or the like. The catheter distal end 7 rests within the bladder 8 when the catheter apparatus 1 is in position for use.

A drainage lumen 10, for passage of fluid from the bladder 8, through the catheter apparatus 1, and into the drainage bag 3, is housed within the tube 5. A plurality of apertures 11 provide for flow communication between the bladder 8 and the drainage lumen 10.

The drainage lumen 10 has a proximal end 12 connecting to a drainge valve assembly 13. In the embodiment illustrated in FIGS. 1 through 10, the proximal end 12 connects to the drainage valve assembly 13 through a flared and flexible silicone adapter 14 with an inside diameter increasing in width toward the drainage valve assembly 13.

The drainage valve assembly 13 has a first end 15 and a second end 16. As shown, the first end 15 is matingly tapered to be sealably received by the flexible adapter 14 and the second end 16 is tapered to be sealably received into an elastically pliable end 17 of the drainage line 2. The drainage lumen apertures 11 are thus fluid flow connected with the drainage bag 3 except as selectively occluded by the valve assembly 13.

Figures 2, 3, 4:
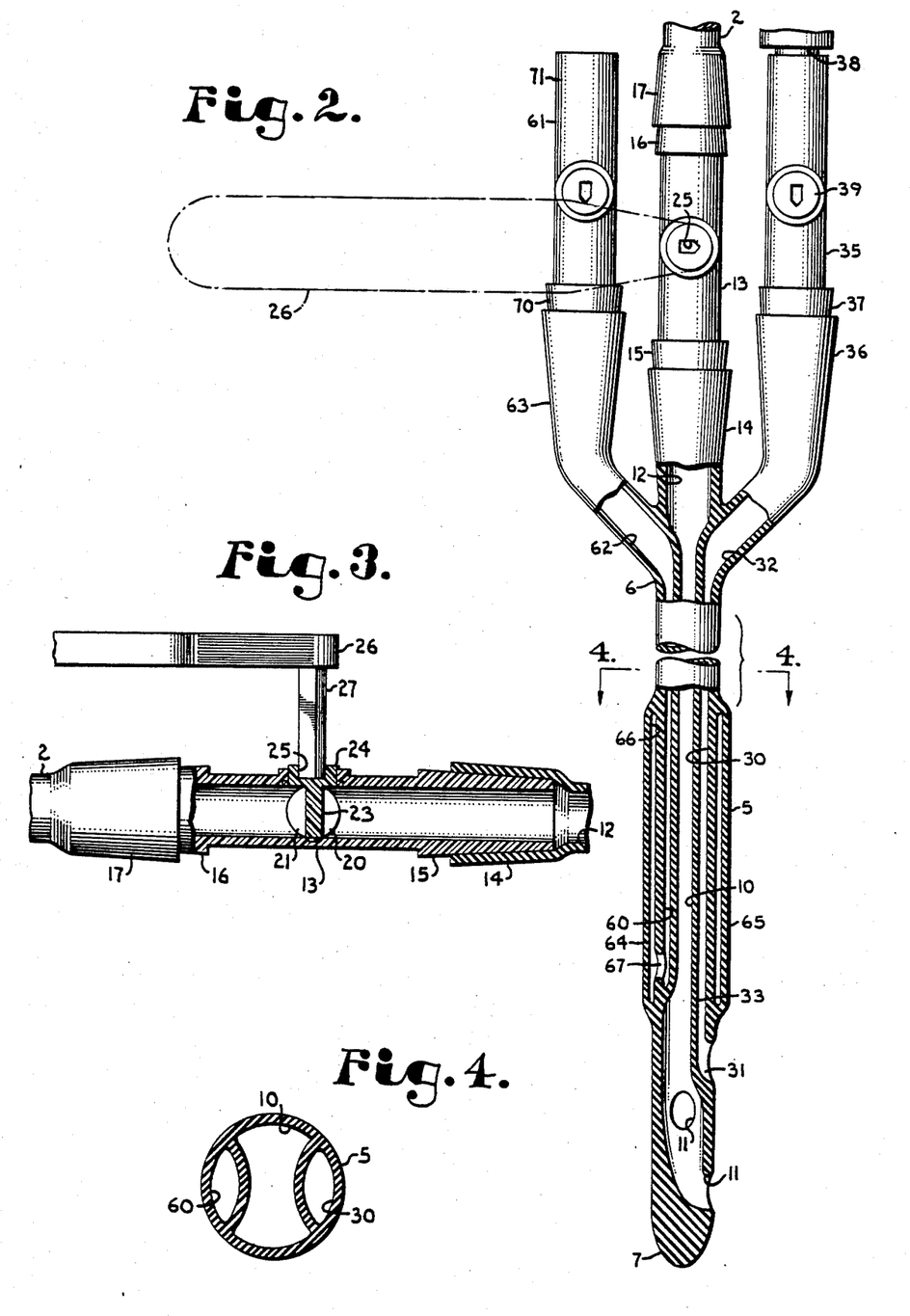
FIG. 2 is an enlarged fragmentary top plan view of the catheter apparatus with portions broken away to illustrate internal detail.
FIG. 3 is a fragmentary side elevational view of the catheter apparatus showing a drainage lumen thereof and showing details of a valve member associated with the drainage lumen.
FIG. 4 is a further enlarged transverse cross-sectional view of the catheter apparatus taken along line 4—4 of FIG. 2 and illustrating internal lumina thereof.

As best seen in FIG. 3, the the drainage valve assembly 13 has a valve 20 having a closed position and an open position. When valve 20 is in the closed position, the drainage valve assembly 13 prevents drainage of fluid 18 from the bladder 8. When the valve 20 is in the open position thereof, the drainage valve assembly 13 allows free flow of fluid from the bladder 8, through the drainage lumen 10 and into the drainage bag 3. As shown, the drainage valve 20 comprises a butterfly valve member 21 having a generally round or disc-like shape with a rotation axle or stem 23 running through the center of the disc and in a plane parallel to faces of the disc and sealably extending externally of the interior of the drainage line 2.

The drainage valve 20 is selectively positioned by a drainage valve actuator 24. The valve actuator 24 is that portion of the rotation stem 23 which integrally and coaxially extends outwardly from the drainage valve assembly 13. The valve member actuator 24 has therein a distal cavity 25 having a direction indicating shape, see FIG. 2, which is visually indicative of whether the valve member 21 is in the open or closed position thereof. In particular, as seen in FIG. 2, the cavity 25 has a shape, when viewed from above by an attendant, of a polygon having five sides of equal length and two interior angles of ninety degrees, thus defining a generally arrow shaped volume.

The drainage valve actuator 24 is selectively manipulated between open and closed positions of the valve 20 by insertion of an actuator tool 26, having a lug 27 thereon which snugly mates with the cavity 25, into the cavity 25 and thereafter rotating the drainage valve member 21 through a ninety degree rotation by means of leverage applied by the tool 26 in rotating. The tool 26 is selectively and easily removable from the cavity 25 after use therein. Because the actuator tool 26 is required to turn the drainage valve member 21, unintended blockage of or tampering with the drainage valve assembly 13 is substantially avoided. Blockage of the drainage line 2 in a patient for too long can result in damage to the bladder 8 and patient trauma. Similarly, failure to properly occlude or block the drainage line 2 prior to proper irrigation of the bladder 8 can result in insufficient treatment of the bladder 8 of the patient. The actuator cavity 25 and tool 26 arrangement, ensures that an undesirable blockage or opening of the drainage line 2 can not easily occur due to tampering by untrained personnel.

An irrigation lumen 30 is also housed within the tube 5. An aperture 31 provides flow communication between the irrigation lumen 30 and the bladder 8.

The irrigation lumen 30 has a proximal end 32 and a distal end 33. The proximal end 32 connects to an irrigation valve assembly 35 and the distal end 33 opens into the aperture 31. The proximal end 32 of the irrigation lumen 30 flares outwardly to facilitate connection thereof to the irrigation valve assembly 35 which is inserted therein. In particular, the irrigation lumen proximal end 32 has a flexible silicone adapter 36 with an inside diameter increasing in width in that portion of the adapter 36 nearest the irrigation valve assembly 35.

The irrigation valve assembly 35 has a first end 37 and a second end 38. Preferably, the first end 37 is tapered to mate with and be received into the flexible adapter 36 at the proximal end 32 of the irrigation lumen 30.

The irrigation valve assembly 35 includes a valve 39 having an open position and a closed position. When the valve 39 is in the closed position thereof, the irrigation lumen 30 is effectively blocked to prevent the introduction of irrigant fluid into the bladder 8. When the valve 39 is in the open position thereof, the irrigation lumen 30 is open to allow the flow of irrigant into the bladder 8.

The valve 39 has a valve member 46 and a shaft 47 terminating so as to define a cavity 48. The valve 39 is selectively actuated in the manner described for the drainage valve assembly 13 by the same actuator tool 26 used in cavity 48 as is used in the cavity 25.

The irrigation valve assembly second end 38 is removably connected to an irrigation source or intermediate reservoir 49, shown as a flexible solution bag in FIG. 1. It is foreseen that the irrigation reservoir 49 may also be a syringe or the like suitable to contain irrigant rather than the bag shown. The reservoir 49 is lockably connected to the irrigation valve assembly 35 to ensure that a leakproof connection is made therebetween and to prevent unintended disconnection. In the present embodiment, a quick connect locking mechanism 50 is shown of the type sold under the tradename Luer-lok, although other types of quick connect devices could be alternatively used. The locking mechanism 50 has two disconnectable portions shown as female portion 51 and male portion 52. Here, the male portion 52 is attached to the irrigant reservoir 49 and comprises a hollow stem 53 surrounded by a threaded flange 54. The female portion 51 is connected to the second end 37 of the irrigation valve assembly 35 and has a lip 55 on the end of the valve assembly 35. The male portion 52 is rotated as it couples with the female portion 51 so as to engage the threaded ridges on the flange 54 of the male portion 52 with the lip 55 on the irrigation valve assembly 35, thus providing an interlocking connection.

It is foreseen that a retention means may be needed to retain the catheter apparatus 1 in the bladder 8. A balloon retention means is depicted in the present embodiment. In particular, a balloon inflation lumen 60 is housed within the tube 5. The inflation lumen 60 has a proximal end 62 connected to an inflation valve assembly 61. As illustrated, the proximal end 62 connects to the inflation valve assembly 61 through a flared, flexible adapter portion 63 with an inside diameter increasing in width as the valve assembly 61 is approached.

The balloon retention means further includes an inflatable balloon 64 of a type well known in the art which wraps about the catheter distal end 7 and is adapted to be inflated within the bladder 8 when positioned therein. The ballon 64 includes a membrane 65 which seals about the tube 5 and defines a chamber 66 therebetween which flow communicates with the inflation valve assesmbly 61 through an aperture 67 communicating with the inflation lumen 60.

The inflation valve assembly 61 has a first end 70 and a second end 71. The second end 71 connects to the proximal end 62 of the balloon inflation lumen 60. The distal end 71 of the inflation valve assembly 61 is tapered to facilitate connection to the flared adapter portion 63.

The inflation valve assembly first end 70 selectively and removably connects to an inflation syringe 72. The inflation syringe 72 illustrated has a tapered end 73 which frictionally engages the second end 71 of the valve assembly 61.

The inflation valve assembly 61 has a valve member 80 with a rotation shaft and actuator 82 terminating in an end having a cavity 83 therein. The valve 80 and parts thereof are similar in structure and operation to drainage valve 20 and are selectively actuated with the tool 26.

It is foreseen that to further ease operation of the catheter system A the three valve assemblies 13, 35 and 61 may be color coded. Preferably, the drainage valve assembly 13 is color coded yellow, the irrigation valve assembly 35 orange, and the inflation valve assembly 61 blue. Further, the mechanism in each case for connecting to the side of the various valve assemblies 13, 35 and 61 on the side thereof opposite the tube 5 is different in either size or shape to prevent accidental connection to the wrong valve assembly. It is also foreseen that the actuator tool 26 would preferably be marked in a manner, such as with arrows, indicating the direction of movement for opening and closing the valves.

A kit for the irrigation and drainage of a bladder according to the present invention comprises the catheter apparatus 1 previously described, the irrigation intermediate source 49, illustrated as a bag but alternatively being a syringe or the like, the actuator tool 26, the inflation syringe 72, a reservoir refill container of irrigant 81 having a valve assembly 82 operably positioned to block flow through a conduit 83 providing flow communication with the interior of the container 81 when the valve assembly 82 is open and being suitable for joining with the irrigation source 49. The valve assembly 82 is also actuated by the actuator tool 26 to allow refilling of the source 49 from the container 81.

Figure 8:
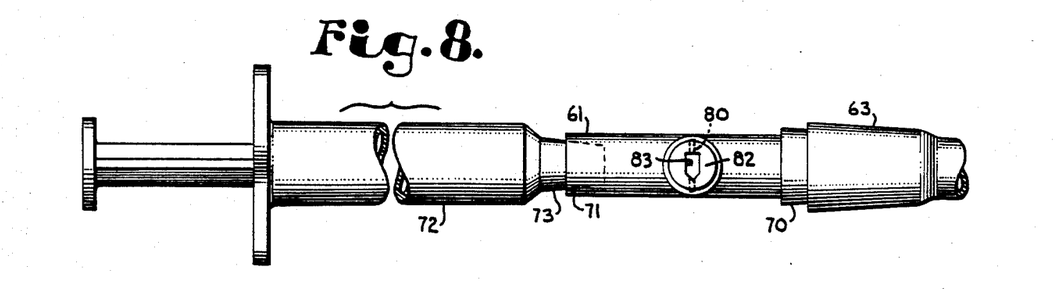
FIG. 8 is an enlarged and fragmentary top plan view of the catheter apparatus showing the retention balloon valve assembly and a balloon syringe.

The catheter apparatus 1 is described in use as a bladder irrigation and drainage apparatus. In such use, the distal end 7 of the catheter apparatus 1 is inserted into a urethra 9 until the membrane 65 of the balloon 64 is completely encompassed by the bladder 8. The inflation valve assembly 61 is then opened with the actuator tool 26, the balloon syringe 72 is connected to the inflation valve assembly 61, as shown in FIG. 8, and the balloon 64 is inflated. The inflation valve assembly 61 is closed before the inflation syringe 72 is disconnected therefrom, such that the balloon 64 remains inflated. The drainage valve assembly 13 is opened by turning the drainage valve actuator 24 to the open position thereof with the actuator tool 26. Similarly, the irrigation valve assembly 35 is already closed.

Figure 6:
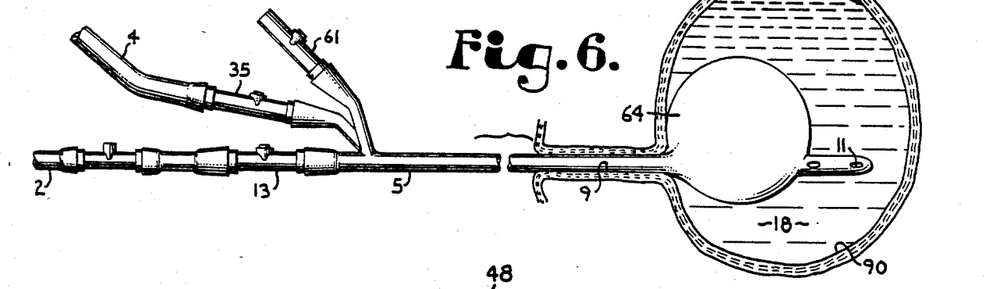
FIG. 6 is a view of the catheter similar to FIG. 5 immediately following administration of an irrigant into the bladder.
Figures 7, 9:
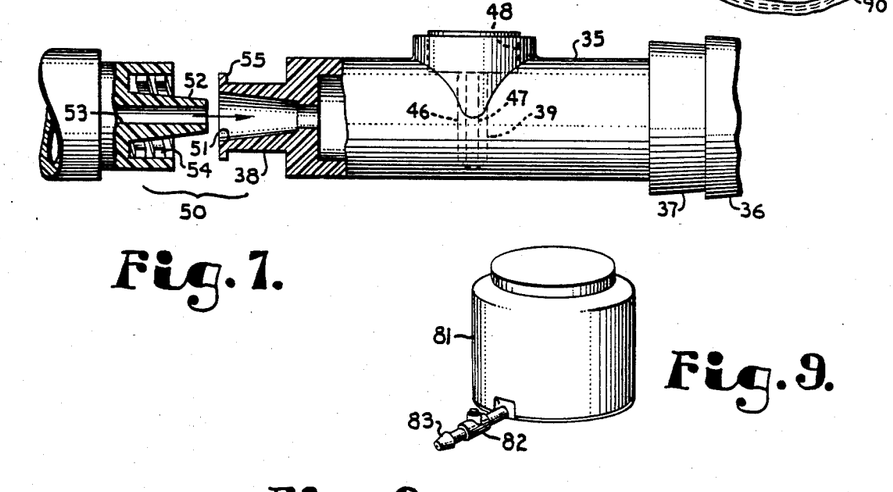
FIG. 7 is an enlarged fragmentary side elevational view of the catheter showing an irrigation valve assembly with portions broken away to illustrate a mechanism for connecting an irrigant source thereto.
FIG. 9 is a perspective view of an irrigant supply reservoir for use in a kit including the catheter apparatus of FIG. 1.

While the catheter apparatus 1 is serving a drainage function, it is left as described in the previous paragraph with the drainage valve assembly 13 open, so as to allow drainage of urine from the bladder 8 to the drainage collection bag 3. When an irrigation of the bladder 8 is desired, the irrigation reservoir 49, filled with a preselected volume of an irrigating fluid. Thereafter the reservoir 49 is connected to the irrigation valve assembly 35 by means of the locking mechanism 50. The drainage valve assembly 13 is then closed by turning the drainage valve 20 to the closed position thereof with the actuator tool 26, thereby preventing further drainage of fluid 18 from the bladder 8. Similarly, the irrigation valve assembly 35 is opened. The irrigant, preferably a solution containing iodine, is then allowed to flow into the bladder 8 resulting in a distended bladder wall 90 as shown in FIG. 6 such that the solution contacts the entire bladder mucosae. FIG. 5 shows the catheter apparatus 1 and bladder immediately prior to the flow of irrigant thereinto and FIG. 6 illustrates the catheter apparatus 1 and bladder 8 immediately following filling of the bladder 8 with irrigant.

Following the flow of irrigant into the bladder 8, the irrigation valve assembly 35 is closed, leaving the irrigant in the bladder 8. The irrigation reservoir 49 is then disconnected from the irrigation valve assembly 35, as desired. A preferred antiseptic iodine solution having a concentration of iodine in the range of from approximately 0.01% to 0.10%, especially 0.05%, by weight iodine is used as the irrigant and has relatively mild side effects with respect to human tissue. The irrigant is retained in the bladder 8 for approximately one minute to ensure asepsis. After the desired retention time, the irrigating fluid is drained from the bladder 8 by re-opening the drainage valve assembly 13. The drainage valve assembly 13 is left open to permit continual drainage of the bladder 8. A column of irrigant is left in the irrigating lumen 30 so as to promote asepsis therein and to prevent contamination of the bladder 8 with infectious matter which could enter the lumen 30 during manipulation of the valve assembly 35.

It is foreseen that the irrigant reservoir 49 may alternatively be filled to a volume somewhat greater than that normally held by the bladder 8 to be irrigated, for example 500 milliliters of irrigant solution to be placed in the reservoir 49 by connection to the irrigation reservoir 81 through the connecting conduit 83. The reservoir 49 is then suspended approximately 30 inches above the bladder 8 at which time the valve assembly 13 is closed and the valve assembly 35 is opened. Irrigant is allowed to flow into the bladder 8 until the bladder 8 is distended by the pressure of the fluid acting therein and the bladder mucosae is in full contact with the solution. The irrigant is retained for approximately one minute and then the valve assembly 35 is closed and the valve assembly 13 is opened to allow drainage of the bladder 8. The reservoir 49 is then disconnected from the valve assembly 35.

Figures 10, 11, 12:
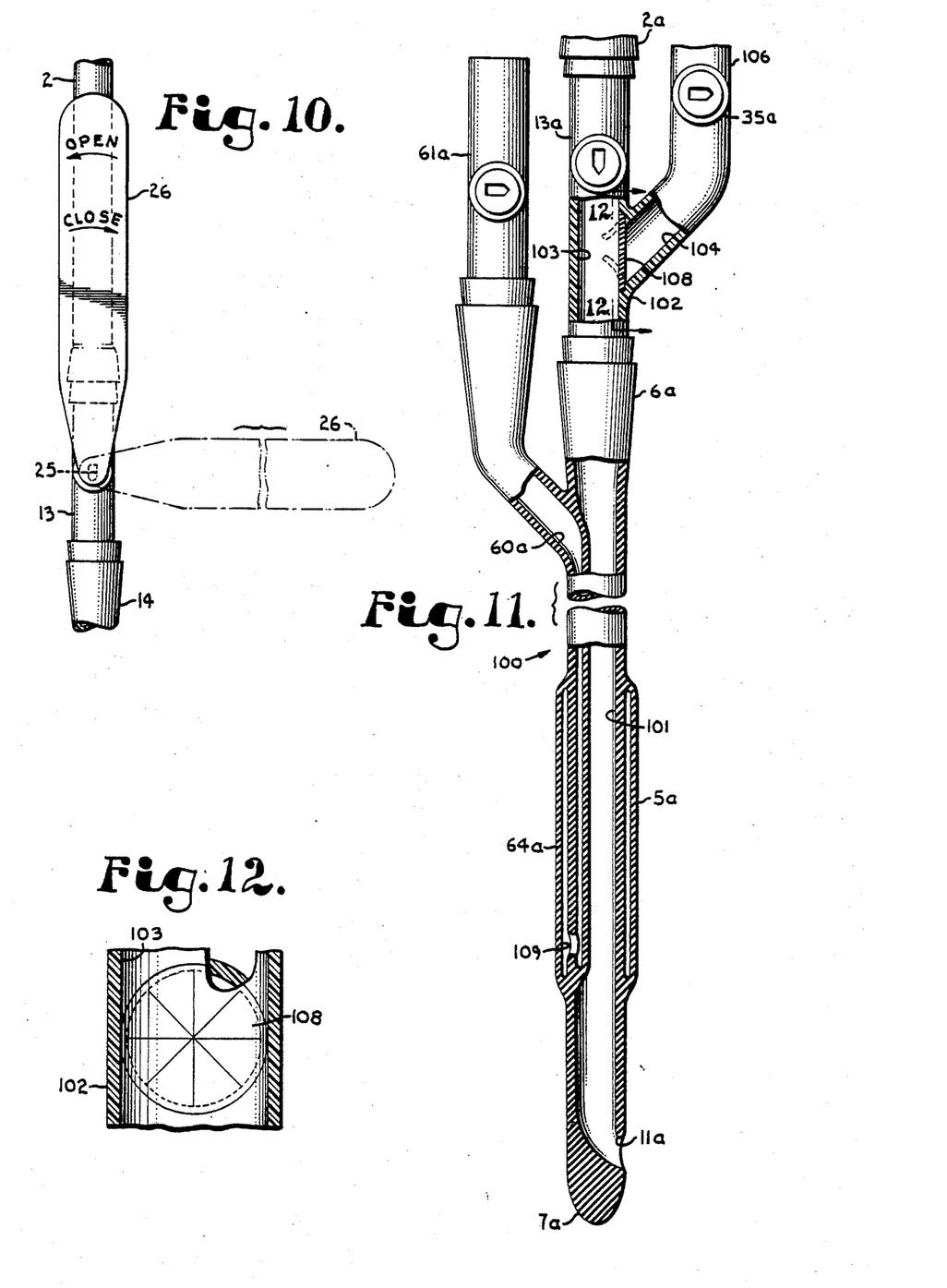
FIG. 10 is an enlarged and fragmentary top plan view of an irrigation lumen and valve assembly with a valve actuator connected thereto in an open position and showing the actuator in a closed position in phantom.
FIG. 11 is a top plan view of a modified catheter apparatus according to the present invention with portions broken away to show detail thereof.
FIG. 12 is an enlarged and partial cross-sectional view of the modified catheter showing a restrictive orifice, taken along line 12—12 of FIG. 11.

A second or modified embodiment of a catheter according to the present invention is illustrated in FIGS. 11 and 12 and generally designated by the reference numeral 100. The catheter 100 is similar to the catheter of the apparatus 1 and similar parts of catheter 100 and apparatus 1 are numbered with the same numeral except the former includes the prefix "a".

The catheter 100 includes an elongate tube 5a having a proximal end 6a and a distal end 7a. The tube 5a includes a drainage and irrigation lumen 101 passing axially therethrough and opening through aperture 11a externally of the tube 5a near the distal end 7a. The lumen 101 is operably connected to a three-way or Y-shaped conduit 102. The conduit has diverging passageways 103 and 104 opposite the lumen 101. The passageway 103 is operably connected to a drainage line 2a through a valve assembly 13a. The passageway 104 is operably connected to an irrigant source conduit 106 through a valve assembly 35a. The conduit 106 may be in communication with an irrigant source (not shown).

A restrictive orifice 108, as best seen in FIG. 12, is frictionally expanded outwardly under pressure to allow irrigant to flow into the lumen 101 but to elastically return to a closed position when the valve assembly 35a is closed so as to operably maintain a column of irrigant between the lumen 101 and the valve assembly 35a.

A retention balloon 64a is positioned about the tube 5a near the distal end 7a and has an interior inflatable cavity 109 which is connectable through a lumen 60a and an inflation valve assembly 61a for connection with an inflation device (not shown) such as a syringe.

In operation, the catheter 100 is similar to apparatus 1 except that the single lumen 101 is utilized for both irrigation and drainage. During irrigation the valve assembly 35a is opened and the valve assembly 13a is closed. During drainage the relative positions of the valve assemblies 13a and 35a is reversed.

The following are examples of methods of practice utilizing the apparatus and methods described herein. These examples are provided to allow one having ordinary skill in the art to practice the inventions described herein and are not meant to be limiting.

EXAMPLE 1

An aqueous solution containing 0.01% iodine by weight was used to examine the efficacy of iodine as an antiseptic on common bacteria and yeasts. A one milliliter aliquot of the iodine solution was added to a one milliliter sample of the microorganisms in a solution containing a minimum of 10 million ($10^7$) organisms per milliliter. The samples of the microorganisms were made to a McFarland standard. Following the addition of the iodine solution to the microorganism sample with mixing, a swab was placed in the mixed sample and thereafter passed onto a culture media. In all cases, the period of time between the addition of the iodine solution to the microorganism sample and the plating of the organisms was sixty seconds. All of the microorganisms tested were killed under these reaction conditions. The following bacteria were tested; *Staphylococcus aureus, Pseudomonas aeruginosa, Salmonella, Serratia marcesceus, Escherichia coli,* Klebsiella, Enterobacteriaceae, Enterococcus, Shigella, Atinobacteriaceae, *Proteus vulgaris* 6380, and *Proteus vulgaris* 13315. The following yeasts were also tested: *Candida albicans* and *Torulopsis glabrata.* The tests were conducted at 21 degrees C.

EXAMPLE 2

It is foreseen that a patient to be catheterized would be treated according to the following procedure. A sterile catheter is inserted through the urethral opening and into the bladder utilizing an aseptic technique. The insertion continues until the balloon portion of the catheter is completely contained within the bladder. The valve assemblies are all closed and a drainage collection bag is connected to the catheter. The retention balloon is inflated by use of a balloon syringe in conjunction with selective actuation of the balloon inflation valve. The drainage valve is opened thus permitting drainage of urine from the bladder, through the catheter and into the collection bag where it is retained. Immediately following drainage of substantially all urine from the bladder, except for a small amount of urine which is normally residual in the bladder, the bladder is immediately irrigated as described below. If the discharged irrigant contains debris or is clouded with infectious matter, further, irrigations are performed until there is no longer any visible debris or infectious matter in the fluid draining from the bladder. Periodically, preferably every eight hours, the drainage collection bag is emptied through a drain located therein, but, where possible, the catheter drainage line and collection bag are never disassembled from the catheter.

Thereafter, every eight hours, immediately prior to the emptying of the drainage collection bag, an irrigation of the bladder is performed with an antiseptic. Where the patient is a normal adult, for each irrigation a reservoir containing two hundred and fifty milliliters of 0.05% iodine solution by weight in normal saline and including 0.1% potassium iodide by weight is connected to the irrigation valve assembly. The drainage valve is closed and the irrigation valve opened. The irrigation solution is allowed to flow into the bladder. The irrigation valve is closed and the irrigation solution is retained within the bladder for a period of one to two minutes. The drainage valve is then opened and the fluid allowed to drain from the bladder into the drainage collection bag thereby consequently sterilizing the fluid in the collection bag.

Immediately prior to removal of the catheter from the patient, the bladder is again filled with irrigant and the balloon is deflated. The catheter is then removed before the bladder is drained. Preferably, sufficient irrigant is left in the patient to trigger a desire to void. The patient then voids, flushing the irrigant from the bladder and sterilizing the urethra with the irrigant.

EXAMPLE 3

In a patient suffering from cystitis the following treatment is utilized. The catheter is inserted into the bladder as in Example 2. The bladder is rinsed several times in rapid succession with the iodine irrigant solution, again as in Example 2 except as noted below, until the bladder is considered cleansed of the drainage from the cystitis and has only a brownish iodine tint. Each time the iodine solution is retained within the bladder for a period of one minute. A 1% by weight amount of pyridium is added to the iodine solution before flowing into the bladder and acts as an anesthetic to ease patient discomfort from the catheter and from infection in the bladder which was present prior to insertion of the catheter. After the drainage remains free of debris and infectious matter, the catheter is then removed, using the irrigation procedure for a final rinse of the urethra with the antiseptic iodine solution.

EXAMPLE 4

The patient is treated in the same manner as in Example 2 except initially a first amount of about 125 milliliters of irrigant is allowed to pass into the bladder, held about one minute and drained. In this process residual urine in the bladder is mixed with the first amount of irrigant and substantially flushed from the bladder while iodine oxidizing constituents of the remaining urine are generally neutralized. Thereafter, an additional amount of about 125 milliliters of irrigant is allowed to pass into the bladder, held about one minute and drained. This process is repeated every eight hours in addition to just after catherization and prior to removal of the catheter.

EXAMPLE 5

The patient is treated in generally the same manner as in Example 2 except the irrigation reservoir is filled with about 500 milliliters of irrigant. The reservoir is suspended approximately 30 inches above the bladder with the catheter drainage valve closed and the catheter irrigation valve open such that irrigant flows due to gravity into the bladder. This is continued until flow ceases and held for about one minute. Thereafter, the drainage valve is opened and the irrigation valve is closed so as to allow the irrigant in the bladder to pass through the drainage tube into the drainage collection bag.

EXAMPLE 6

An apparatus as shown in the illustrated embodiments is inserted into the bladder. The irrigation valve assembly is operably connected to a source of dye suitable for a cystogram and which source is suspended about 30 inches above the bladder. The drainage valve assembly is closed and the irrigation valve opened. Dye is allowed to flow into the bladder until distended so as to allow the bladder to be visualized. The dye is thereafter drained by opening the drainage valve assembly and closure of the irrigation valve assembly.

EXAMPLE 7

The procedure according to Example 6 except that the dye has added thereto iodine and sodium iodide sufficient to provide about 0.05% iodine by weight therein.

EXAMPLE 8

A cystoscopy is performed on a patient. Thereafter, a catheter as described in the illustrated embodiments herein or a Robinson catheter is inserted into the urethra and bladder. An irrigant solution of about 0.02% by weight iodine is allowed to pass into the bladder through a lumen in the catheter retained for three minutes after which the catheter is withdrawn. The patient is then told to void so that the irrigant sterilizes the urethra.

EXAMPLE 9

Prior to surgery on the colon, an enema is given. Thereafter, a catheter in accordance with the catheters described in the embodiments of the invention above is anally inserted into the colon. an irrigant solution comprising approximately 0.05% by weight iodine is allowed to pass through the catheter irrigation valve into the colon and retained for 5 minutes therein. Thereafter, the irrigant is drained by opening the drainage valve assembly and the catheter is removed. The catheter can also be used while inserted in the colon to perform a barium enema to visualize the interior of the colon.

EXAMPLE 10

In a patient undergoing peritoneal dialysis, the dialysis solution has added thereto a saline solution with iodine therein sufficient to produce a concentration of 0.0005% by weight iodine in the solution. The solution is retained in the peritoneal cavity for the normal duration.

EXAMPLE 11

A nasogastric tube is emplaced in a patient prior to gastro-duodenal surgery when the patient has a gastric ulcer, is achlorahidric or has gastric carcinoma. A solution comprising about 0.01% iodine is passed through the tube and retained for several minutes. The tube is then aspirated. A solution remaining in the stomach or intestines after aspiration may be removed at the time of surgery.

Examples 12 and 13 are hypothetical at the time of filing.

EXAMPLE 12

Dialysis solutions were prepared including one part iodine in a ratio to 50,000; 100,000; 200,000; and 400,000 parts of dialysis solution by weight. The solutions were each divided into four aliquots each of which had added thereto *Staphylococcus aureus, Pseudomonas aeruyinoa, Escherichia coli* and Streptococcus respectfully such that about from 1,000 to 10,000 of such microorganisms were present per milliliter. After 15 minutes a sample of each solution was placed in a culture dish with culture media and tested for bacterial growth. All of the cultures showed no microorganism growth.

EXAMPLE 13

A saline irrigant solution was prepared comprising 0.05% iodine with suitable concentrations of sodium iodine. Multiple samples were prepared containing 30 milliliters of urine to which were added the various microorganisms discussed in Example 1 to a level of at least $10^7$ microorganisms per milliliter. To each sample of urine and microorganisms was added 125 milliliters of the irrigant solution. After 1 minute another 125 milliliters of the irrigant solution was added to each solution and then after one minute a swab was passed through the samples and passed onto culture media to test for microorganism growth. In each case there was no growth recorded and thus all microorganism samples were sterilized by the irrigant solution.

It is to be understood that while certain forms of the present invention have been illustrated and described herein, it is not to be limited to the specific forms or arrangement of parts described and shown.

What is claimed and desired to secure by Letters Patent is as follows:

1. A method of promoting asepsis of a living human urinary bladder; said method comprising the steps of:
    (a) introducing an antiseptic solution into said bladder;
        (i) said antiseptic solution being a solution having a concentration of iodine ranging from approximately 0.0002% to 7% by weight;
        (ii) said solution further including glycol in a range from approximately 1% to 40% by weight;
    (b) retaining said antiseptic solution within said bladder until asepsis occurs; and,
    (c) draining said antiseptic solution from said bladder.

2. The method according to claim 1 wherein:
    (a) said glycol is present in a concentration of about 20% by weight.

3. The method as set forth in claim 1 wherein:
    (a) said solution contains pyridium in a concentration of about 1% by weight.

4. The method according to claim 1 wherein:
    (a) said glycol is present in a concentration of about 20% by weight.

5. A method of promoting asepsis of a living human urinary bladder; said method comprising the steps of:
    (a) introducing an antiseptic solution into said bladder;
        (i) said antiseptic solution being a dilution of Lugol's solution having a concentration of iodine ranging from approximately 0.0002% to 7% by weight; said Lugol's solution is substantially the only source of iodine in said solution; said solution includes glycol in a range of from approximately 1% to 40% by weight;
    (b) retaining said antiseptic solution within said bladder until asepsis occurs;
    (c) draining said antiseptic solution from said bladder.

6. A method of promoting asepsis of a living human urinary bladder; said method comprising the steps of:
    (a) introducing an antiseptic solution into said bladder;
        (i) said antiseptic solution being a dilution of Lugol's solution having a concentration of iodine ranging from approximately 0.0002% to 7% by weight; said Lugol's solution is substantially the only source of iodine in said solution; said solution contains pyridium in a concentration of about 1% by weight;
    (b) retaining said antiseptic solution within said bladder until asepsis occurs; and
    (c) draining said antiseptic solution from said bladder.

* * * * *